May 6, 1969 M. HAGERSTROM Plant Pat. 2,884
STRAWBERRY PLANT
Filed Aug. 28, 1967
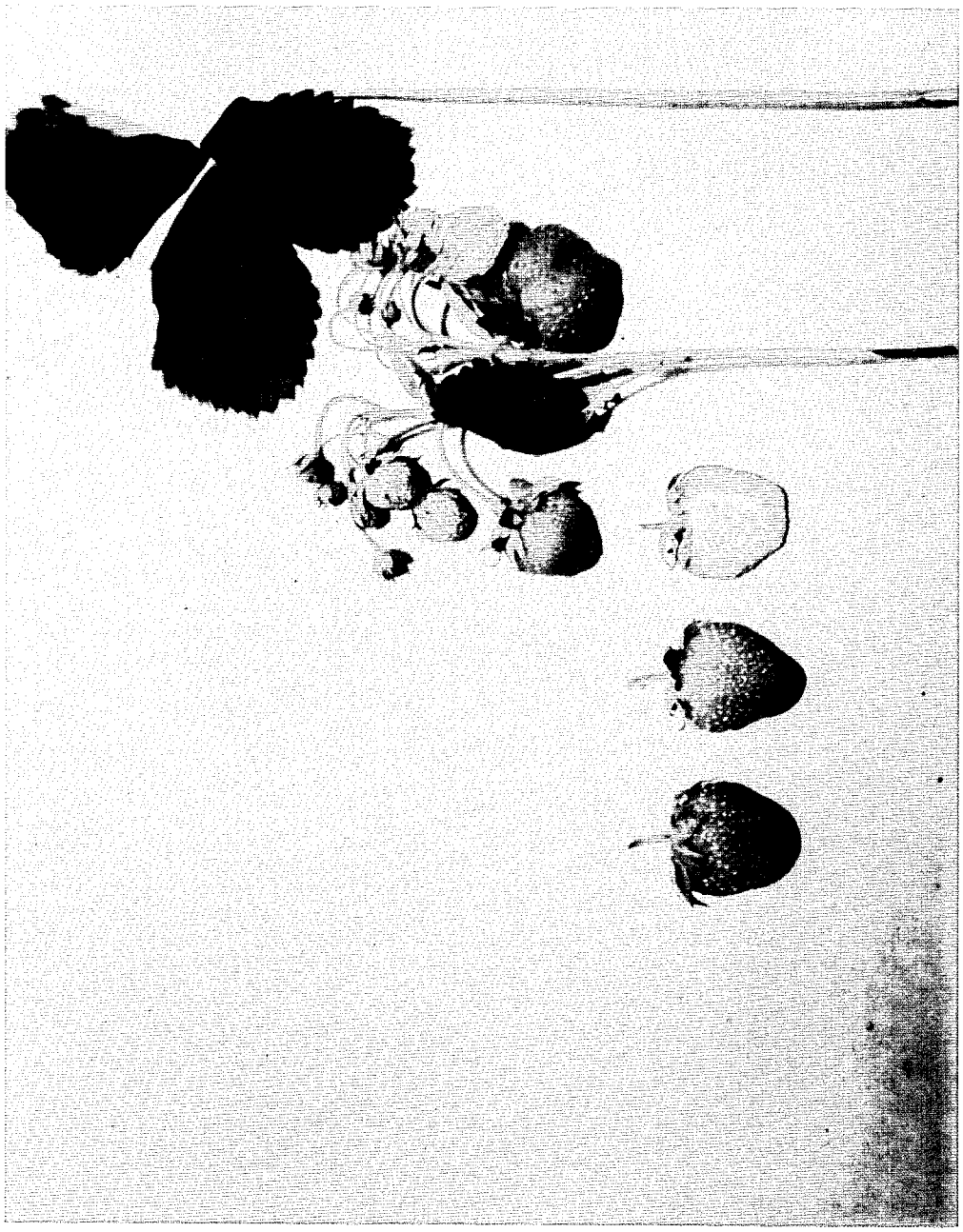
Inventor.
Marion Hagerstrom
By: Robb & Robb
Attorneys.

United States Patent Office

Plant Pat. 2,884
Patented May 6, 1969

2,884
STRAWBERRY PLANT

Marion Hagerstrom, Monticello, Minn., assignor to Stark Bro's Nurseries & Orchards Co., Louisiana, Mo., a corporation of Missouri

Filed Aug. 28, 1967, Ser. No. 663,904
Int. Cl. A01h *5/08*
U.S. Cl. Plt.—48 1 Claim

The present invention relates to a new and distinct variety of strawberry plant which was originated by me by crossing the variety known as "Red Rich" Plant Patent No. 993, expired, with the variety known as "Midland" (unpatented).

As the result of this breeding, I have produced a new and improved variety of strawberry plant which is distinguished from its parents, as well as from all other varieties of which I am aware, as evidenced by the following unique combination of characteristics which are outstanding therein:

(1) A general resemblance to the variety known as the Christ strawberry (Plant Patent No. 1,365), sold commercially under the registered trademark "Starkrimson" of Stark Bro's Nurseries & Orchards Co., but having more vigorous and hardier habits of growth;

(2) A more productive fruit-bearing habit; and (3) More attractive berries of very high quality resembling those of the Christ variety, but being more uniformly large in size throughout the picking season and having a sweeter flavor.

Asexual reproduction of my new strawberry variety by runners, as performed by me at Monticello, Minn., shows that the foregoing characteristics and distinctions come true to form and are established and transmitted through succeeding propagations.

The accompanying drawings shows typical specimens of the fruit and foliage of my new variety, with the fruit specimens shown in various stages of development and including mature fruit specimens in elevation and in axial cross-section, all as depicted in color as nearly true as it is reasonably possible to make the same in a color illustration of this character.

The following is a detailed description of my new strawberry variety, with color terminology in accordance with Nickerson's Color Fan, published by Munsell Color Company, Inc., of Baltimore, Md., except where general color terms of ordinary dictionary significance are obvious:

Location where grown and observed: Monticello, Minn.
Dates of first and last pickings: June 18 and June 30, respectively.
Plant:
- *Growth.*—Vigorous.
- *Root.*—Vigorous.
- *Crown.*—Simple; large size.
- *Leaves.*—Many; large size. Petiole: Long; stout; petiole of central leaflet equals that of the lateral, and blade of central leaflet equals lateral. Color—Dark Green, Hue 5GY 4/3 tinged with red on exposure; with bracts. Pubescence—abundant; spreading. Groove—shallow. Serrations—irregular, with teeth broadly ovated-ciliate on margin and having green apex; serrations of both central and lateral leaflets extend over upper ¾ of margin. Leaflets: Upper surface—glossy; smooth; flat; color—Moderate Olive Green, Hue 5GY 4/3. Lower surface—color—light green. Pubescence—scant.
- *Runners.*—Appear during fruiting; numerous; stocky.
- *Flower stems.*—Medium short; inflorescence protected by foliage.

Bloom: Medium lateness.
- *Date of first bloom.*—May 20.
- *Date of full bloom.*—June 6.
- *Flowers.*—Many; perfect. Breadth: primary—1½ inches; secondary—1⅜ inches. Filaments of stamens—short. Pollen—abundant.

Fruiting stems: From long to medium length; stout; upright.
- *Radical.*—Shorter than main truss
- *Branches of truss.*—Few.

Soil where grown: Sandy loam; well drained.
Culture: Mulched with straw.
Fruit:
- *Condition when described.*—Prime; date June 20.
- *Size.*—Fairly uniform; large; nearly constant throughout season. Average length—1¼ inches. Average breadth 1⅛ inches. Average thickness 1 1/16 inches.
- *Form.*—Uniform; regular; obtuse-conical; apex rounded.
- *Stems.*—Radical—medium stout; long. Main truss stout.
- *Calyx.*—Even with surface; medium free; large; green after picking. Upper surface: color—Light Green, Hue 5GY 5/6; pubescence—abundant. Lower surface: color—Light Green, Hue 5GY 5/6; pubescence—scant. Segments—from 11 to 15: length—½ inch; breadth—¼ inch; form—oval; acute. Epicalyx—wanting.
- *Surface.*—Glossy. Color—Strong Red, Hue 5R 4/12.
- *Seeds.*—Many; conspicuous; depressed below surface; many small fertile lower seeds. Color—Strong Greenish Yellow, Hue 10Y 8/11. Markings—none.
- *Core.*—Some solid and some hollow. Color—white center, surrounded by Vivid Red, Hue 5R 5/13.
- *Flesh.*—Juicy. Color—Vivid Red, Hue 5R 5/13. Texture—firm; fine.
- *Flavor.*—Subacid; rich.
- *Quality.*—Best. Shipping quality—good.
- *Use.*—Market; dessert.

I claim:

1. A new and distinct variety of strawberry plant, substantially as herein shown and described, characterized particularly as to novelty by the unique combination of a general resemblance to the variety known as the Christ strawberry (Plant Patent No. 1,365), sold commercially under the registered trademark "Starkrimson" of Stark Bro's Nurseries & Orchards Co., but having more vigorous and hardier habits of growth, a more productive fruit-bearing habit, and more attractive berries of very high quality resembling those of the Christ variety, but being more uniformly large in size throughout the picking season and having a sweeter flavor.

No references cited.

ROBERT E. BAGWILL, *Primary Examiner.*